United States Patent [19]
Fleega

[11] Patent Number: 5,827,300
[45] Date of Patent: Oct. 27, 1998

[54] SET OF MEDICAL INSTRUMENTS FOR PLACING AND SHIFTING KNOTS DURING SURGERY

[76] Inventor: Basim A. Fleega, Theaterplatz 26, D-53117 Bonn, Germany

[21] Appl. No.: 693,057

[22] PCT Filed: Feb. 18, 1995

[86] PCT No.: PCT/EP95/00592

§ 371 Date: Aug. 19, 1996

§ 102(e) Date: Aug. 19, 1996

[87] PCT Pub. No.: WO95/22931

PCT Pub. Date: Aug. 31, 1995

[30] Foreign Application Priority Data

Feb. 25, 1994 [DE] Germany .......................... 44 06 203.6

[51] Int. Cl.⁶ .................................................. A61B 17/04
[52] U.S. Cl. ............................ 606/148; 606/139; 289/17
[58] Field of Search ..................... 606/148, 139, 606/144; 289/1.2, 17

[56] References Cited

U.S. PATENT DOCUMENTS

| | | | |
|---|---|---|---|
| 5,192,287 | 3/1993 | Fournier et al. ....................... | 606/139 |
| 5,234,444 | 8/1993 | Christoudias ........................... | 606/148 |
| 5,292,327 | 3/1994 | Dodd et al. ............................. | 606/148 |
| 5,334,200 | 8/1994 | Johnson ................................. | 606/148 |
| 5,403,330 | 4/1995 | Tuason ................................... | 606/148 |
| 5,501,691 | 3/1996 | Goldrath ................................ | 606/148 |
| 5,549,618 | 8/1996 | Fleenor et al. ......................... | 606/148 |
| 5,562,684 | 10/1996 | Kammerer ............................. | 606/139 |
| 5,601,576 | 2/1997 | Garrison ................................ | 606/148 |

FOREIGN PATENT DOCUMENTS 5192338  1/1992  Japan ..................................... 606/148

*Primary Examiner*—Michael Powell Buiz
*Assistant Examiner*—Tina T. D. Pham
*Attorney, Agent, or Firm*—Antonelli, Terry, Stout & Kraus, LLP

[57] ABSTRACT

A set of medical instruments for placing and shifting knots produced with surgical sutures during surgery, wherein a further through bore is provided for pulling a suture through in the vicinity of the head end of the rod, said bore being located transversely with respect to the lengthwise axis of the cylindrical rod, with the head end of the cylindrical rod being designed as a knot shifter for shifting and tightening a knot produced by means of the sutures. Using the knot shifter and knot cutter proposed according to the invention, a reliable knotting and hence immobilization of the parts rejoined by surgical sutures, such as tendons, to their original fastening areas can be achieved.

5 Claims, 14 Drawing Sheets

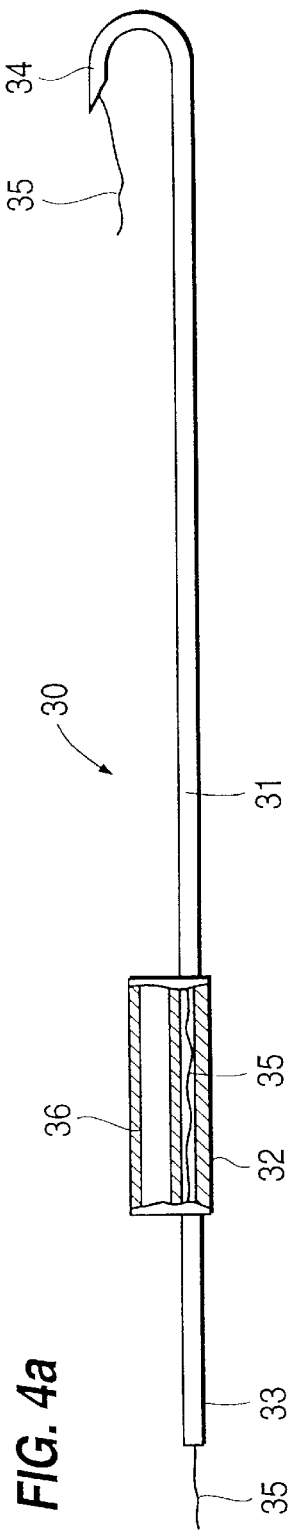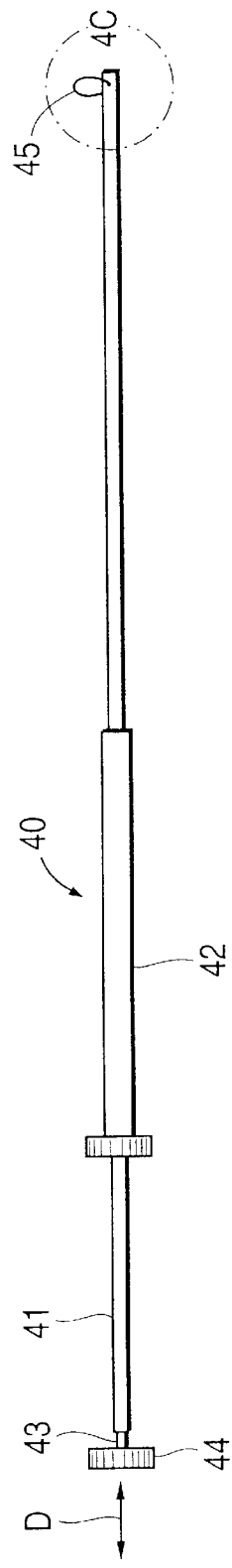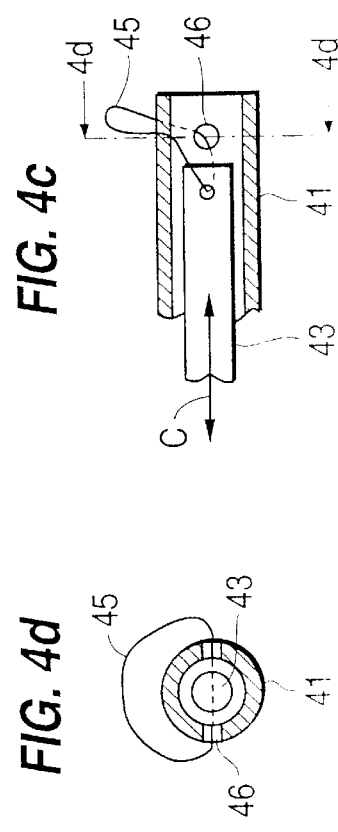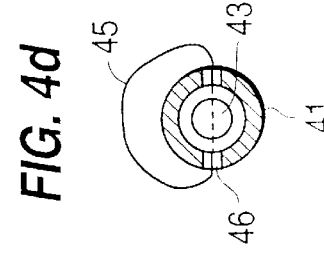

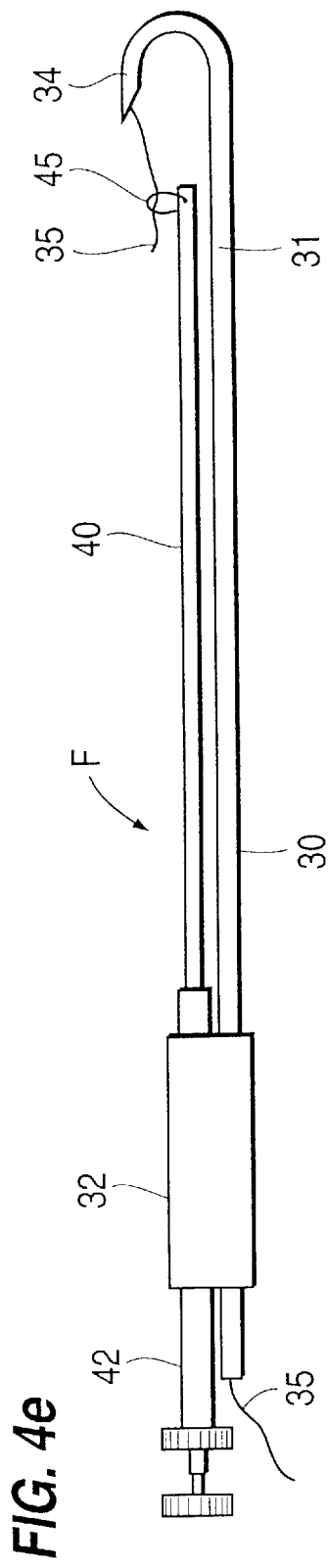
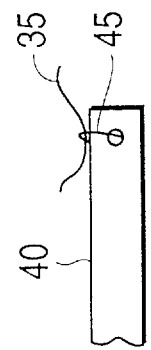

SET OF MEDICAL INSTRUMENTS FOR PLACING AND SHIFTING KNOTS DURING SURGERY

BACKGROUND OF THE INVENTION

1. Field of the Invention

The invention relates to a set of medical instruments for shifting and placing knots produced in surgical sutures during surgery. Surgery of this kind, in which sutures are placed and knotted and must then be brought to certain locations, occurs for example, during the reconstruction of a tear of the rotator cuff in which tendons must be sutured.

2. Background Art

In conventional reconstruction of a tear of the rotator cuff, it has always been necessary heretofore to open the involved portion of the patient's shoulder over a relatively large area to create sufficient room for the operation. Operations within such large areas however always involve very high stress on the patient and require a correspondingly long period of convalescence.

Efforts have therefore been made to perform surgery as transarthroscopic surgery with correspondingly small surgical incisions, so that the disadvantages of conventional surgical methods are avoided. To perform such transarthroscopic surgery and reconstruction, even with the consequence of suturing tears, require however correspondingly adapted and new instruments in order to be able to perform the tasks required, even in correspondingly small surgical incisions.

SUMMARY OF THE INVENTION

The goal of the present invention is to provide a set of medical instruments for performing transarthroscopic reconstruction surgery of an tear of the rotator cuff for example, in which sutures are placed, knotted, pulled tight, and brought to the correct location.

As a set of medical instruments for placing and shifting knots produced in surgical sutures during operations, the invention proposes an arrangement characterized in that it contains a cylindrical rod displaceable lengthwise in a cylindrical sleeve, said rod projecting beyond the sleeve at both ends, with said rod having a head end that can be pulled into the sleeve and a gripping end that can be struck externally at the other end of the sleeve, and the head end of the cylindrical rod is designed as a knot shifter for shifting and tightening a knot produced in the suture, and the sleeve end into which the rod can be retracted is designed as a knot cutter with a cutting edge in order to separate the suture ends from the knots.

With the knot shifter and knot cutter proposed according to the invention, reliable knotting and hence immobilization of parts such as tendons reattached by surgical sutures to their original fastening surfaces can be accomplished.

Advantageous embodiments of the instruments according to the invention, which serves as a knot shifter and knot cutter, can be derived from the characterizing features of the subclaims. In particular, the cylindrical rod is designed as a knot shifter with a convexly rounded head end, with two through bores extending from the head end, through which bores a suture can be pushed to the cylindrical jacket surface of the rod. These two continuous bores serve so to speak as needle eyes, with one suture end being pushed through each. Preferably, these two through bores used as needle eyes are formed diametrally opposite one another on the head end of the rod, with the bores extending diagonally from the end of the rod to the jacket surface. These two continuous bores used as needle eyes are relatively small and short, particularly 2–4 mm long with a diameter of 1–2 mm. In addition, the knot shifter and knot cutter according to the invention is provided with an additional through bore for pulling a suture through in the vicinity of the head end of the cylindrical rod, said bore being arranged transversely with respect to the lengthwise axis of the cylindrical rod in such fashion that they do not touch the bores that serve as needle eyes. The transverse through bore is preferably located slightly below the outlets of the two bores starting at the head end on the cylindrical jacket surface of the rod and shortly below the latter. In order to avoid rubbing a suture as it is pulled through the transverse bore, it is proposed that the transverse bore be rounded in the inlet area or outlet area at the cylindrical jacket surface of the rod, at least in the areas that face away from the head end of the rod. It is also proposed that the transverse bore have a diameter slightly larger than that of the two diagonal bores that serve as needle eyes, said bores departing from the head end. The diameter of the transverse bore can be between 3 and 4 mm.

A set of surgical instruments for performing transarthroscopic reconstruction surgery, for example on a tear of the rotator cuff, comprises primarily a bone needle, a tendon needle, straight arthroscopy scissors, the knot shifter and knot cutter according to the invention, a suture layer and catcher, a tendon raspatory, and a bone needle holder.

In order to perform the reconstruction of the tear of the rotator cuff, tendons that have been avulsed must be reattached to their original locations using suitable surgical sutures. For this purpose, a suture layer and catcher is provided that can be composed of two elements mounted displaceably with respect to one another, with one element being designed as the suture layer and the other as the suture catcher. The suture layer is made in the form of a straight continuous hollow needle, bent into the shape of a hook at the end, through which a suture can be passed, and has a permanently attached guide cylinder in the straight part of the needle, which has a through bore through which the suture catcher can be passed. The through bore permits the suture catcher to be guided essentially parallel to the straight part of the suture layer.

The suture catcher comprises a hollow outer cylinder for passing through the through opening of the suture layer and an inner cylinder that is displaceable lengthwise in the hollow cylinder. A wire loop attached to the inner cylinder is guided outward through openings in the outer hollow cylinder and can be placed against the outer surface of the hollow cylinder or moved away from the latter by moving the inner cylinder along the hollow cylinder.

The knot shifter and cutter according to the invention is used for reliable knotting and attachment of the tendon areas rejoined by surgical sutures to their original mounting locations.

With the aid of the knot shifter and cutter of the instruments according to the invention, it is possible to knot the two ends of a surgical suture outside the surgical incision and to feed the ends of the knots through the through bores provided in the cylindrical rod. In this manner, the knot, now located in front of the convex end of the cylindrical rod, can be pushed through the surgical incision until it reaches the desired knotting area in front of the cylindrical rod. By feeding only one end of the suture through a through bore, preferably through the through bore provided in addition to the two through bores that extend to the convex end of the cylindrical rod, a knot pushed forward in this manner can be tightened by pulling simultaneously on both ends of the suture.

In order to cut off the ends of such a placed knot from the rest of the suture close to the knotting location, the invention proposes providing a sharpened area, a cutting edge, to cut the suture that emerges from the holes at the circumference of the cylindrical rod on the lengthwise displaceable cylindrical sleeve on the cylindrical rod of the knot pusher and cutter associated with the instruments according to the invention, at the end of the cylindrical sleeve, facing the end of the cylindrical rod.

A complete set of instruments for performing surgical transarthroscopic reconstruction of a tear of the rotator cuff and its use is described in greater detail in the following with reference to the figures.

BRIEF DESCRIPTION OF THE DRAWINGS

FIG. 2b is a section along arrows AA in FIG. 2a;

FIG. 3b is a section along arrows BB in FIG. 3a;

FIG. 4a is a suture layer in a side view;

FIG. 4b is a suture catcher in a side view;

FIG. 4c is a section through detail X in FIG. 4b;

FIG. 4d is another view of detail X according to section X1—X1 of FIG. 4c;

FIG. 4e is a suture layer and catcher composed of a suture layer according to FIG. 4a and a suture catcher according to FIG. 1b;

FIG. 4f is an enlarged view of the end area of the suture catcher with a suture that has been caught;

DESCRIPTION OF PREFERRED EMBODIMENT(S) OF THE INVENTION

Figure 1:
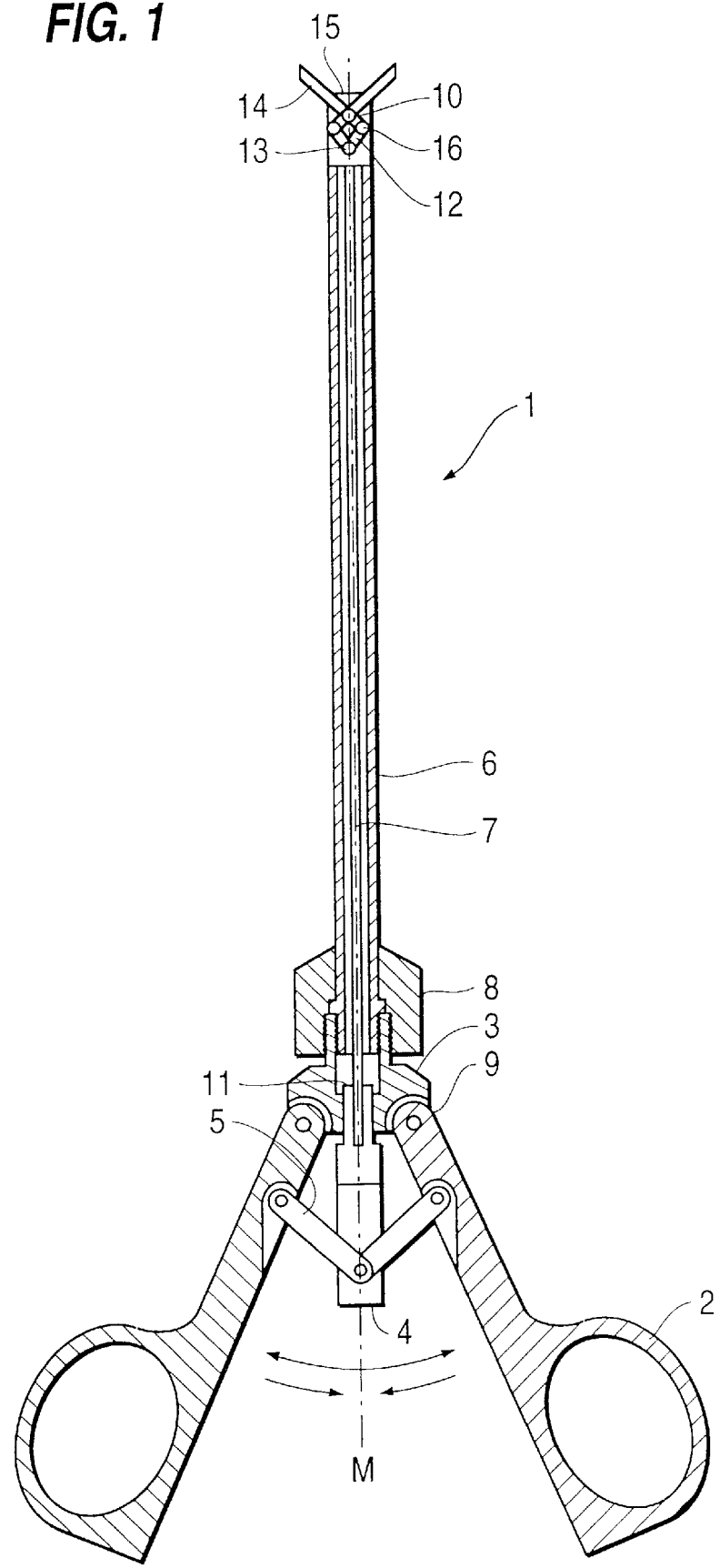
FIG. 1 is a section through a straight scissors for arthroscopy.

According to FIG. 1, the straight arthroscopy scissors 1 of the instruments according to the invention consist of two legs with eye-shaped handles 2, pivotably articulated on pin 9 in scissors bearing 3. An extension 6 in the form of a cylindrical hollow rod is fastened in scissors bearing 3, by screwing or insertion for example, and is fastened by a union nut 8 to scissors bearing 3. The length of extension 6 is determined by the required operating depth. At the other end of the extension, blades 14 are rotatably mounted on a common central axis 10. Extension 6 has a recess 15 at its end for this purpose in order to allow movement of blades 14. The blades are operated by means of handles 2 in such fashion that articulated rods 5 are rotatably mounted on one side on handles 2 and on the other side on a sliding fulcrum 4 which is displaceable in scissors bearing 3. To permit uniform operation of sliding fulcrum 4, the latter is located on the central axis M of straight arthroscopy scissors 1, with articulated rods 5 all having the same length. As a result, both handles 2 are opened or closed to the same degree when sliding fulcrum 4 is displaced. These conditions can be modified depending on the requirement, however.

A tie rod 7 is also attached to sliding fulcrum 4, said rod being displaceable lengthwise in extension 6 along central axis M of straight arthroscopy scissors 1. This tie rod 7 can be screwed into sliding fulcrum 4 by means of a thread 11 for example and thus fastened. By movements of handles 2, known from conventional scissors, sliding fulcrum 4 slides back and forth in scissors bearing 3 as a result of the transmission of force from articulated rods 5 on central axis M, and transmits this movement to tie rod 7 attached to sliding fulcrum 4. At its end facing away from the sliding fulcrum, tie rod 7 has a pin 13 to which additional articulated rods 12 are fastened. These articulated rods 12, together with a sharp cutting part 14, end facing away from pivot point 10, form toggle levers 16 that transmit the reciprocating movement of tie rod 7 to blade parts 14 and permit movement of blades 14. In this manner, it is possible with a suitably selected length of extension sleeve 6 and tie rod 7 to adjust blades 14 of straight arthroscopy scissors 1 to nearly any desired operating depth. Handles 2 can always remain outside the surgical incision.

As is also evident from FIG. 1, the movements of handles 2 and blades 14 are respectively symmetrical mirrorwise to their common central axis M. As a result, the surgeon has especially simple and good control over straight arthroscopy scissors 3 of the instruments according to the invention.

Figure 2A:
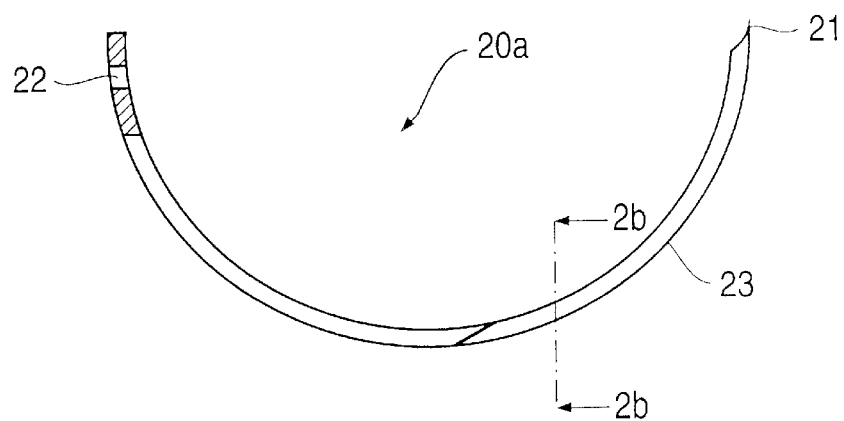
FIG. 2a is a side view of a bone needle.
Figure 2B:
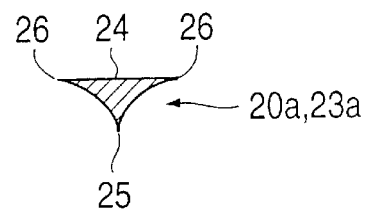

FIGS. 2a and 2b, a tendon needle 20a of the instruments according to the invention. Tendon needle 20a is bent into a semicircle and has at one end a point 21 and at the other end an eye 22 through which a surgical suture can be passed. While it has a preferably round, or at least a rounded, cross section at the end where eye 22 is located, tendon needle 20a, over at least half of its length, starting at needle point 21, has an approximately triangular wedge-shaped cross section 23a as shown in FIG. 2b. Wedge-shaped cross section 23a has a triangular shape delimited by sharpened corners 25 and 26 and flat side surfaces 24. As FIG. 2b also shows, wedge-shaped point 25 of wedge-shaped cross section 23a of tendon needle 20a is located on the outer radius of the semicircular needle.

With this design of the tendon needle, with an approximately triangular wedge-shaped cross section and with the point of the wedge being located on the outer radius of the semicircular needle, permits a considerably improved, easier penetration of the tendon needle into the tendon and produces only minor trauma at the point where it is introduced.

Figure 3A:
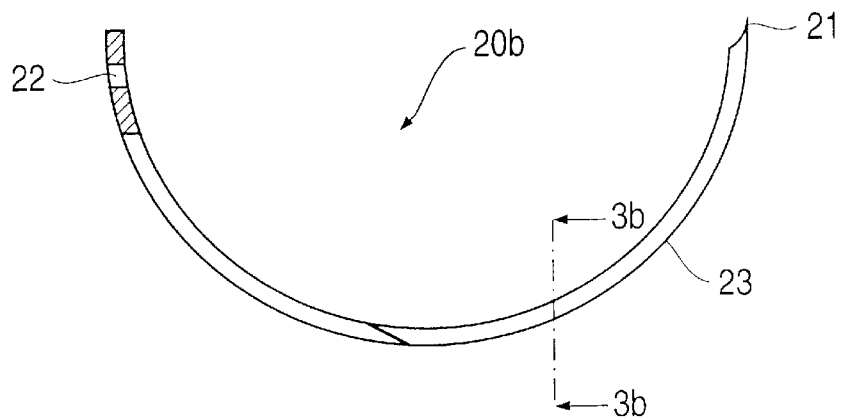
FIG. 3a is a side view of a tendon needle.
Figure 3B:
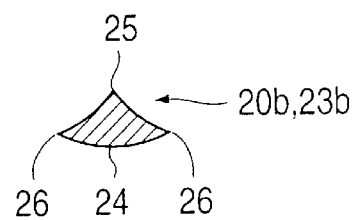

According to FIG. 3a and b, the bone needle of the instruments according to the invention, like the tendon needle described in FIGS. 2a and b, also has a semicircular shape with a point 21 and another end with eye 22 through which a suture can be passed. Once again, the area in which eye 22 is located, preferably with a round cross section but at least a rounded cross section and an approximately triangular wedge-shaped cross section, extends for at least half the length of bone needle 20b, starting from point 21. In contrast to tendon needle 20a described above, however, bone needle 20b of the instruments according to the invention shown in FIG. 3b has an approximately triangular wedge-shaped cross section 23b whose wedge point 25 is located on the inside radius of semicircular needle 20b. This wedge point 25, with its sharpened corners 26 and flat sides 24, approximately delimits triangular wedge-shaped cross section 23b.

A bone needle 20b thus equipped, with a wedge-shaped cross section 23b over at least half its length, starting at point 21, and with wedge point 25 being located on the inside radius of semicircular needle 20b, can be pushed much more easily through bone and can be guided more easily as it passes through the bone.

Suture layer 30 of the instruments according to the invention as shown in FIG. 4a consists of an essentially straight, continuous hollow needle 31, bent in the shape of a hook at one end 34 and provided with a sharpened point. A surgical suture 35 can be pushed from straight end 33 of needle 31 up to point 34 bent in the shape of a hook, from which it then emerges. In addition, a guide sleeve 32 is fastened in the rear area of predominantly straight needle 31 of suture layer 30, said needle having a through bore 36 through which the suture catcher can be pushed. Through bore 36 is aligned to permit essentially parallel guidance of the suture catcher to straight part 31 of suture layer 30.

Suture catcher 40 of the instruments according to the invention as shown in FIG. 4b includes an external hollow cylinder 41 with a thickening 42 mounted thereon for guidance through through bore 36 of suture layer 30 and an inner cylinder 43 that is displaceable lengthwise in hollow cylinder 41. According to FIGS. 4c and 4d, a wire loop 45 is fastened to the end of inner cylinder 43 and guided outward through feedthrough openings 46, as a catching loop for an operational suture. By moving knob 44 mounted on the end of inner cylinder 43 in the direction of arrow D, as indicated in FIG. 4c, inner cylinder 43 moves in the direction of arrow C along outer cylinder 41. Wire loop 45 is then either retracted into the interior of outer cylinder 41 and abuts its surface, or is pushed out of the interior of outer cylinder 41 and forms a catching loop.

If, as indicated in FIG. 4e, suture layer 30 and suture catcher 40 are then pushed together to form a combined suture layer and catcher F of the instruments according to the invention, which entails introducing thickening 42 into through opening 36 of guide cylinder 32, a surgical suture 35 emerging from bent end 34 of the suture layer can be guided through wide-open wire loop 45 of suture catcher 40. After closure of the wire loop as described above and as shown in FIGS. 4b and 4c, the suture is gripped by the wire loop 45 that fits closely against suture catcher 40 and can be pulled further, for example together with suture catcher 40, as shown in FIG. 4f.

Figure 5A:
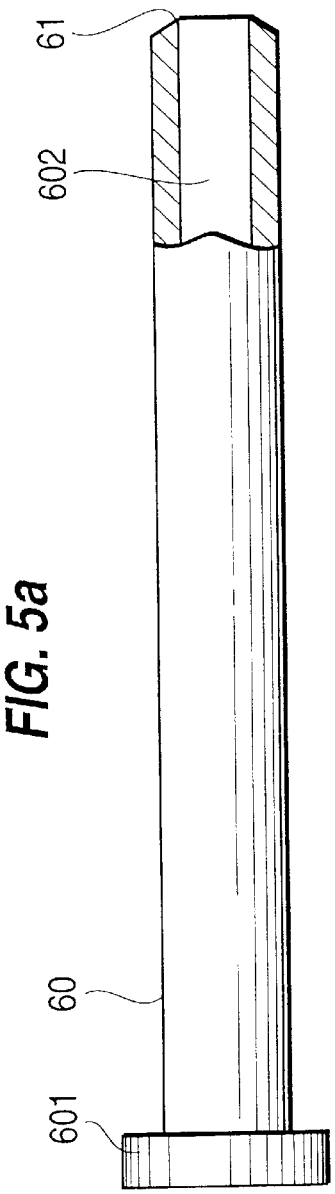
FIG. 5a is a partially cut-away view of a sleeve for a knot shifter and knot cutter.
Figure 5B:
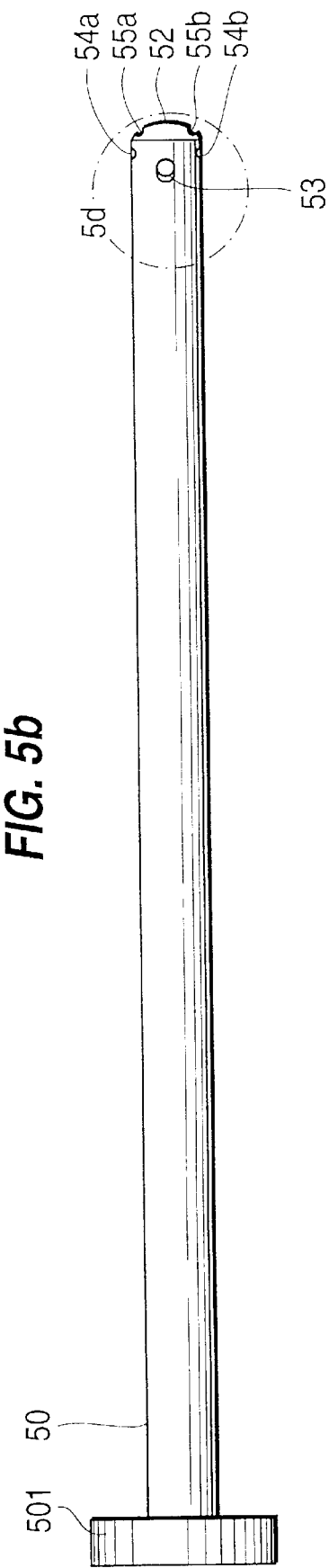
FIG. 5b is a view of the cylindrical rod for a knot shifter and knot cutter.
Figure 5C:
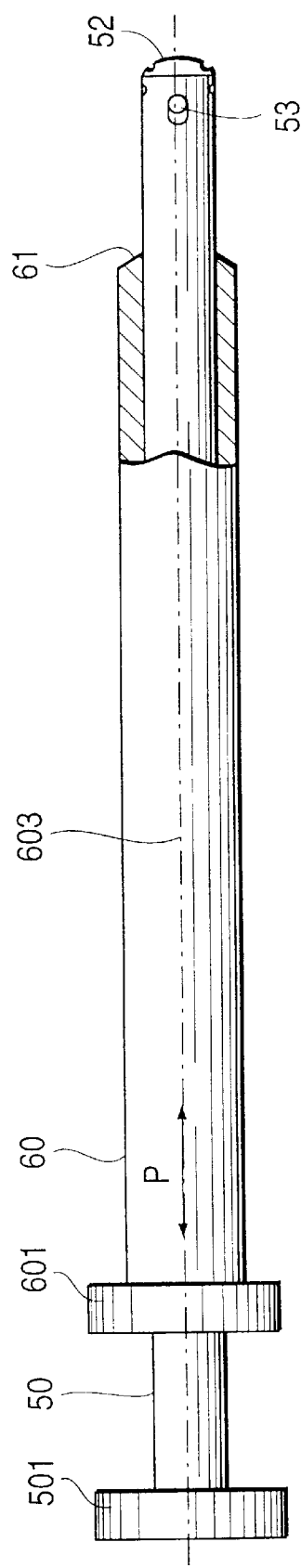
FIG. 5c is a partially cutaway view of the knot shifter and knot cutter composed of the sleeve and the rod according to FIGS. 5a and 5b.
Figure 5F:
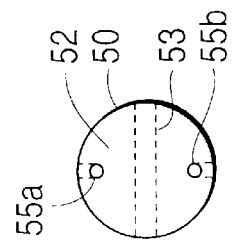
FIG. 5f is a view of the head end of detail Y according to FIG. 5d.
Figure 5E:
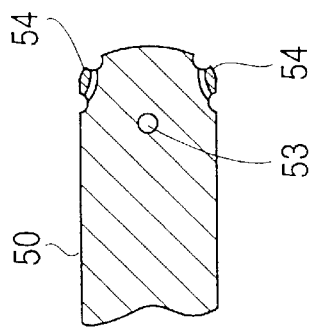
FIG. 5e is a lengthwise section through detail Y according to FIG. 5d.
Figure 5D:
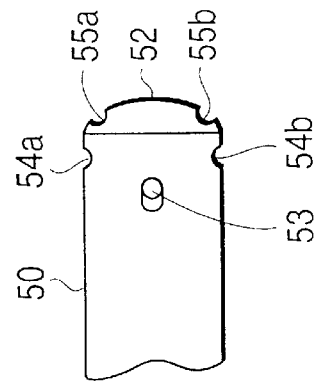
FIG. 5d shows detail Y in FIG. 5b on an enlarged scale.
Figure 5G:
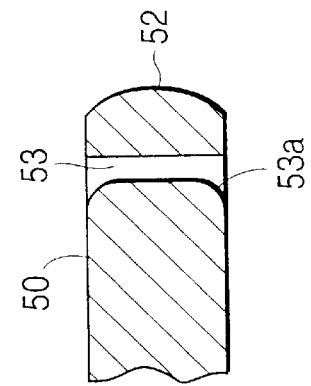
FIG. 5g shows a lengthwise section shifted by 90 degrees through detail Y according to FIG. 5d.

The knot pusher and knot cutter according to the invention, as shown in FIG. 5c, is composed of a cylindrical rod 50 (see FIG. 5b) and a cylindrical sleeve 60 (see FIG. 5a). Cylindrical rod 50, according to FIG. 5b, has at one end a grip 501 in the form of a flanged part and on the other end has a rounded head end 52 with various holes for pulling sutures through and performing various functions. The cylindrical sleeve (see FIG. 5a) has a through bore 602 through which cylindrical rod 50 can be pushed and is displaceable lengthwise in sleeve 60. At one end, sleeve 60 likewise has a grip end with projecting flange part 601 which rod 50 pushed into sleeve 60 can strike (see FIG. 5c) when it is moved along lengthwise axis 603 in the direction of arrow P. At the other end, sleeve 60 (see FIG. 5a) has a surrounding cutting edge 61 that abuts through bore 602. Detail Y, i.e. the head end of cylindrical rod 50 according to FIG. 5b, is shown in the enlarged detailed diagrams in FIGS. 5d–g. Head end 52 of rod 50 is rounded and made convex. From this head end 52, two small bores extend diagonally outward to the cylindrical jacket surface of rod 50 as a through bore through which to pull a suture. These through bores 54, which practically constitute the eye of a needle, have inlet openings 55a and 55b on the ends and outlet openings 54a, 54b on the jacket surface. These holes 54, which are preferably arranged symmetrically opposite one another on the head end, are relatively short and terminate not far from the head end of the rod. In order to permit especially simple passage of a suture through these bores 54, they are made diagonal relative to the lengthwise axis of the rod and to the jacket line of cylindrical rod 50. In addition, an additional through bore is provided in the rod in the vicinity of the head end of rod 50, near outlet openings 54a and b, i.e. transversely with respect to the length of the rod, especially centrally. This bore 53, running crosswise, which can be seen in cross section in FIG. 5g, is preferably made rounded in its entry areas at the jacket surface of cylindrical rod 50, at least in those areas that face away from head end 52 (see roundings 53a).

Figure 5H:
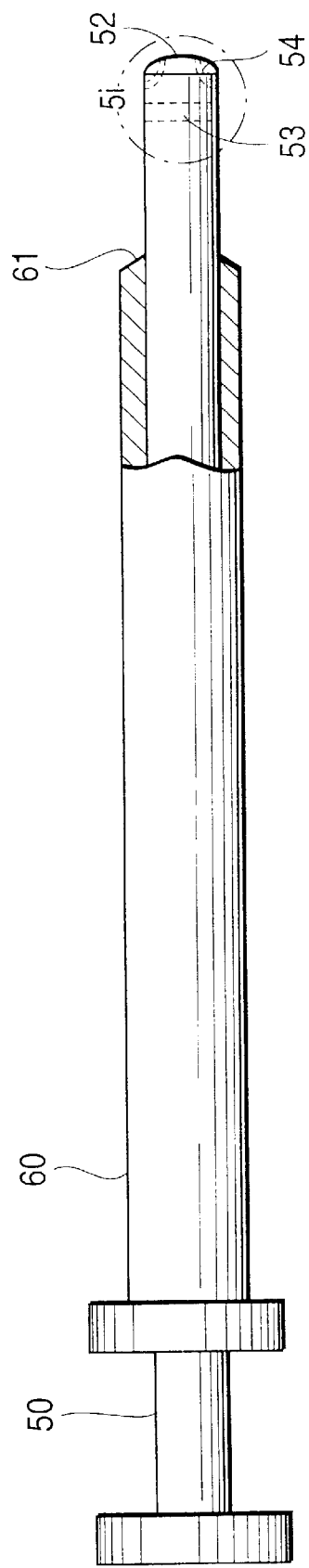
FIG. 5h is another version of a knot shifter and knot cutter according to 5c.
Figure 5J:
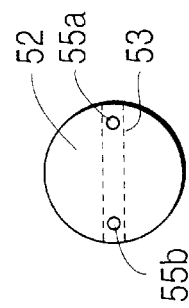
FIG. 5i shows detail Z according to FIG. 5h from a position rotated through 90 degrees.
FIG. 5k is a top view of the head end of detail Z according to FIG. 5i.
Figure 5I:
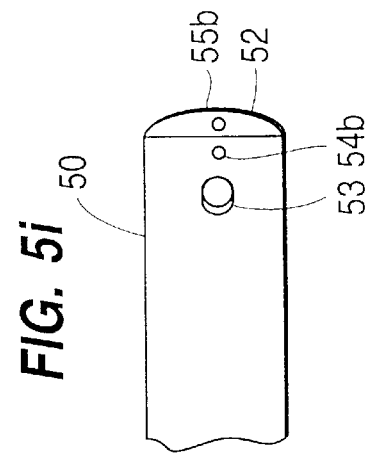

FIG. 5b shows another variation of the knot shifter and knot cutter in which only the arrangement of through bore 53 running crosswise varies by comparison to the cylindrical rod of the knot shifter and knot cutter according to FIG. 5c. Detail Z of cylindrical rod 50 shown enlarged in FIGS. 5i and 5k according to FIG. 5h shows that the through bore is offset 90° relative to the design shown in FIG. 5c.

The knot shifter and knot cutter according to the invention can be used to guide a suture which, for example, has been laid by the suture layer already described and by the suture catcher, through holes 54 and to knot them in front of convexly rounded end 52 of cylindrical rod 50. Upon introduction into the surgical incision in the patient, the knot, then located in front of the end of the cylindrical rod, is pushed in front of the cylindrical rod and can thus be brought into an operating area that is located at a certain depth. To tighten the knot, it is merely necessary to guide one end of the knot through bore 52 and to exert a pull on both ends of the knot to tighten it. Of course, it is also possible to guide one end of the knot through both bores. 54 and then tighten the knot.

To cut a knot tightened in this fashion close to the knotting location to free it of other sutures, cylindrical sleeve 60, which is displaceable lengthwise from the cylindrical rod, has a sharp cutting edge 61 at the end opposite end 52 of cylindrical rod 50. The knot ends which are brought out through continuous bores 54 in cylindrical rod 50 from openings 55 are thus cut when sleeve 60 of sharp edge 61 is advanced at the circumference of cylindrical rod 50.

With the instruments according to the invention, surgical reconstruction of a tear of the rotator cuff is possible by means of a transarthroscopic operation that is much more pleasant for the patient in comparison with the conventional method, which is described below with reference to FIGS. 8a–h.

Figure 8A:
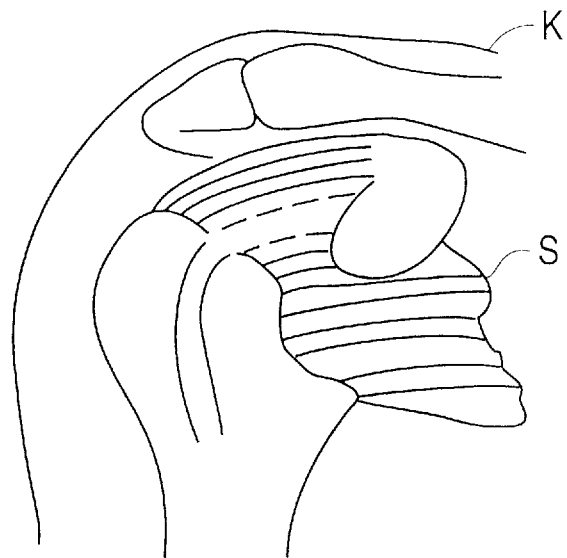
FIG. 8a shows an uninjured part of the shoulder.
Figure 8B:
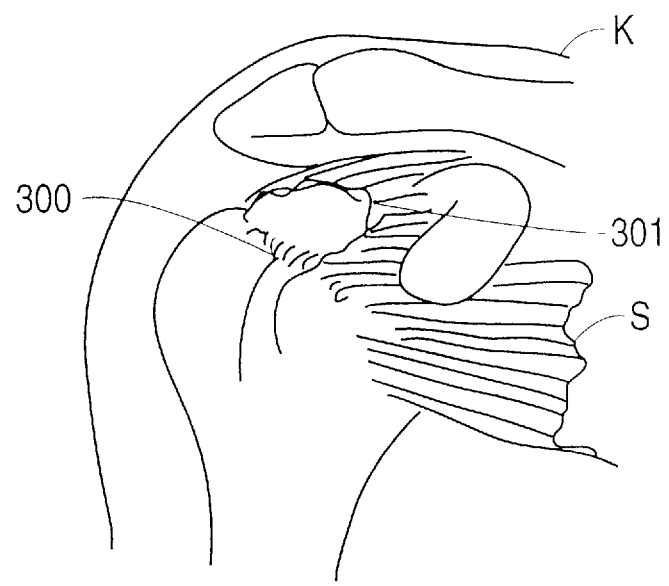
FIG. 8b shows a tear of the rotator cuff
Figure 8C:
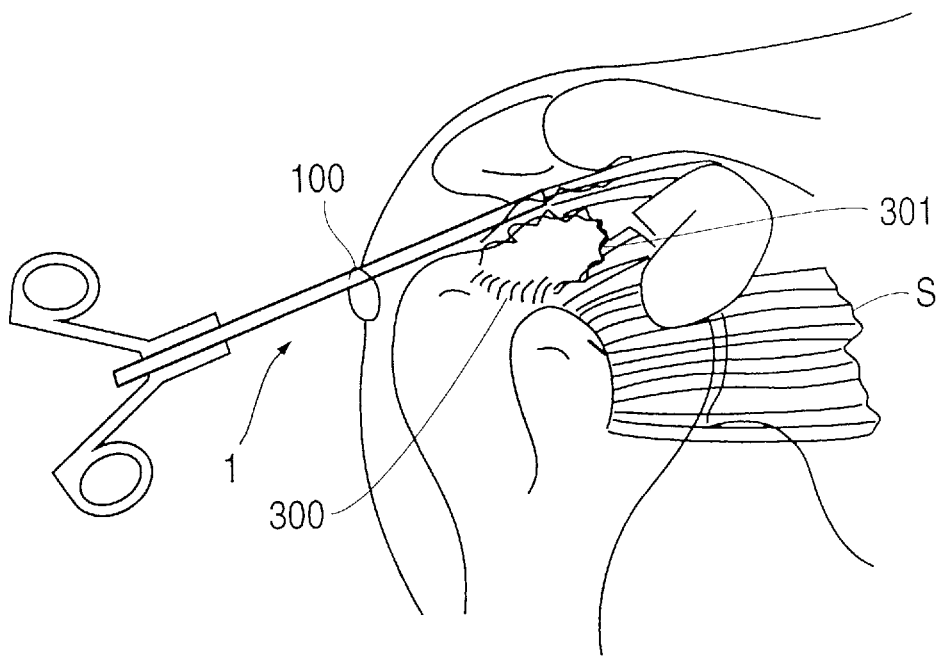
FIGS. 8c–h show in a schematic view the use of the instruments according to the invention in a transarthroscopic surgical reconstruction of a tear of the rotator cuff according to FIG. 8b to create a transossal suture.

FIG. 8a shows the shoulder area of a healthy patient schematically by outlines K, with uninjured tendons S fastened to the bones. In contrast to this illustration, FIG. 8b shows a tear of the rotator cuff in which tendon S is avulsed along a line 301 from its original fastening position 300 on the bone. As shown in FIG. 8c, in preparation for transarthroscopic surgery, an incision 100 is made at a suitable location on body K, through which opening the elements of the instruments according to the invention can be introduced. In a first step, any adhesions of the tendon to the bone are eliminated using straight arthroscopy scissors 1 of the instruments according to the invention. The tendon raspatory of the instruments according to the invention is used to support this effort if the severity of the adhesions warrants. The tendon raspatory is a small metal rasp that is made especially small so that it can be inserted and withdrawn through incision 100. The original location 300 where tendon S was fastened to the bone along its line 301 is prepared for reconstruction by suitable pretreatment using the cutter and raspatory, which essentially means providing a smooth surface and a groove in the bone.

Figure 7A:
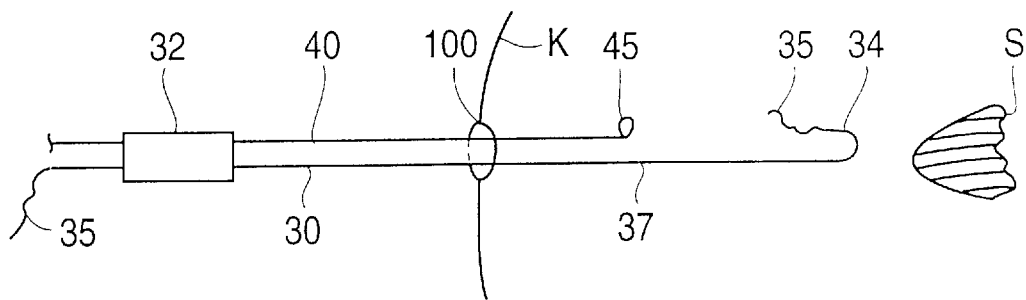
FIGS. 7a–c show the use of the suture layer and catcher in a schematic view.
Figure 7B:
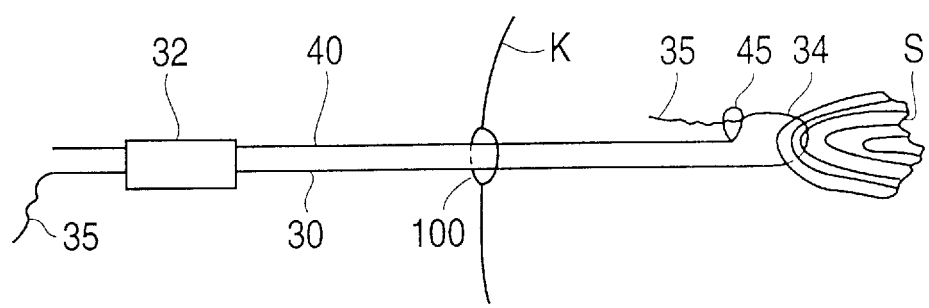
Figure 7C:
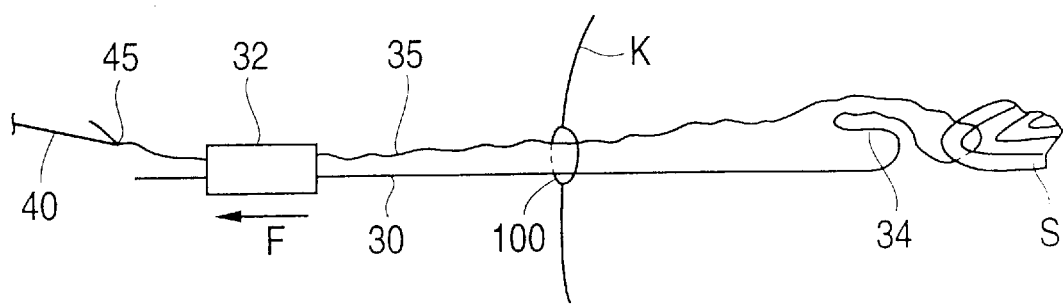
Figure 8D:
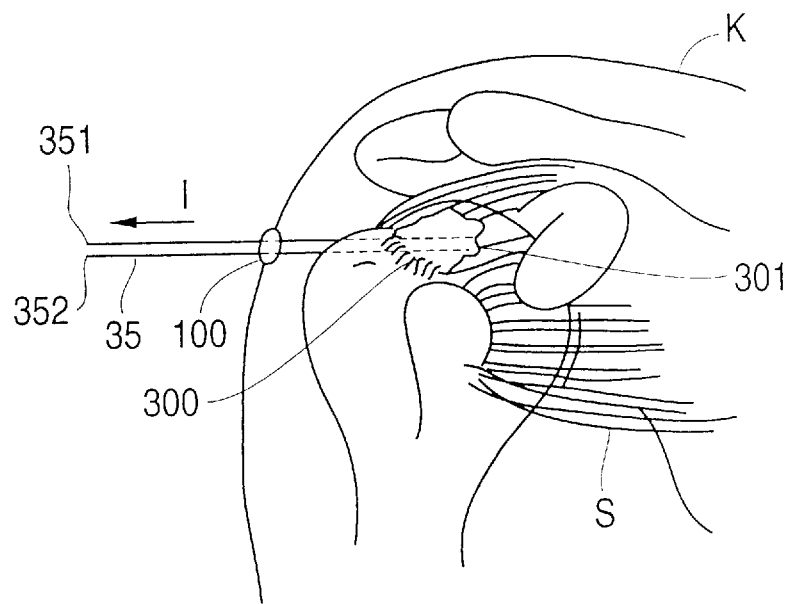
Figure 8E:
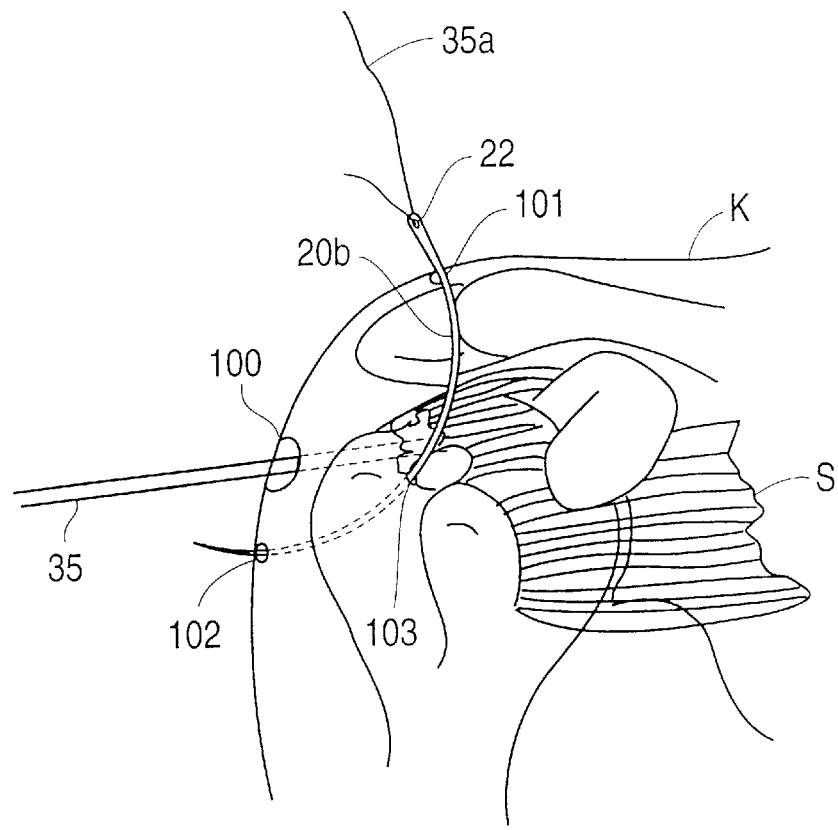

In a next step, using the suture layer and catcher, the tendon is penetrated in area 301 and a suture laid, as shown for example in FIGS. 7a–c. FIG. 7a shows the insertion of hook-shaped end 34 of hollow needle 31 of suture layer 30 with suture 35, which is pulled through hollow needle 31 through the incision in the body and through tendon S, see FIG. 7b. Then suture catcher 40, see FIG. 7b, is pushed further to catch and hold the end of suture 35 with the aid of wire loop 45. The trapped end 35 of the suture is then pulled out of the body with suture catcher 40 in the direction of arrow F, see FIG. 7c. Suture layer 30 is also pulled out of the body so that the two ends 351, 352 of suture 35 are outside the body and the suture is guided through the tendon, see FIG. 8d. Two or three sutures are laid with the suture layer and catcher, said sutures serving to hold the tendon that has been avulsed in position for suturing. These sutures 35 also serve to pull the avulsed tendon into the desired position. FIG. 8d shows the successful laying of such a suture 35 through surgical incision 100 in body K. By pulling in the direction of arrow I, the suture can then be pulled over the bone to its original location 300.

Figure 8F:
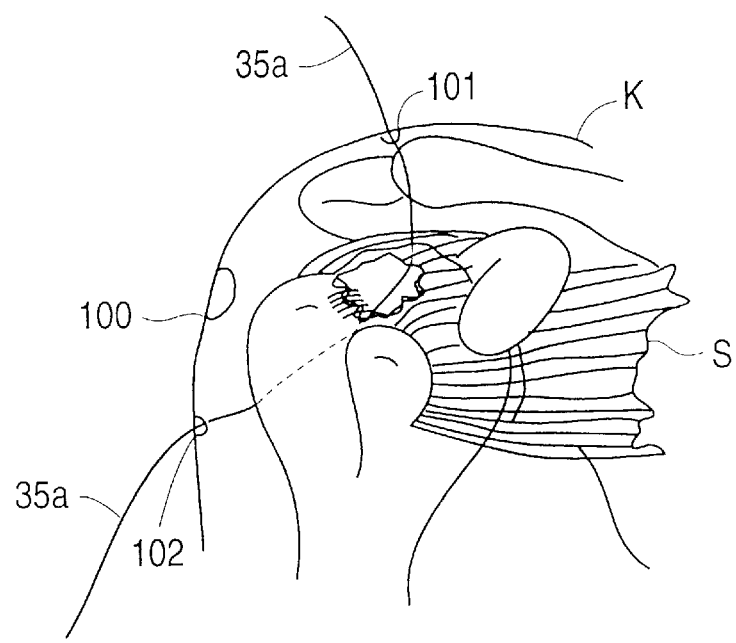

In the next step, the tendon, now held in its original position by means of suture 35 that has been laid, according to FIG. 8a, is penetrated by a bone needle 20b, introduced through another incision 101 in body K, and the bone needle is guided through an incision 103 in the bone and another incision 102 back out of body K. It pulls a suture 35a, which has been pulled through eye 22 of bone needle 20b, behind it along its path through the body so that suture 35a, as shown in FIG. 8f, comes to rest to form a transossal tendon suture. Thus, supporting suture 35, which was previously laid, as shown in FIG. 8d, can be removed once more, so that tendon S snaps back. If the tendon is torn lengthwise, a long special needle, see FIG. 2a, b, that has a concave flattening can be used to pass a suture 35a through the edges of the tear from front to rear as a so-called end-to-end suture.

Figure 6A:
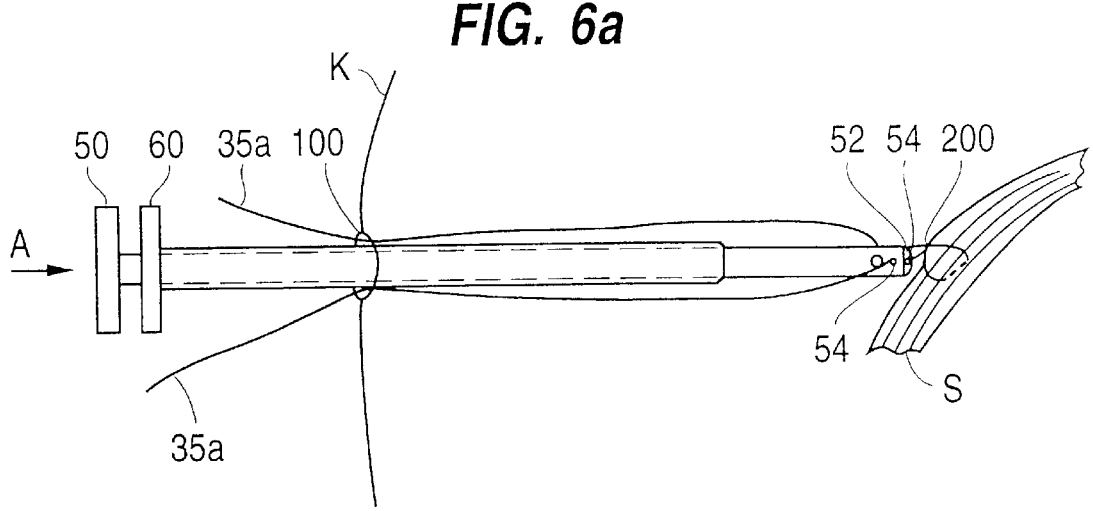
FIGS. 6a–c show a schematic representation of the use of the knot shifter and cutter.
Figure 6B:
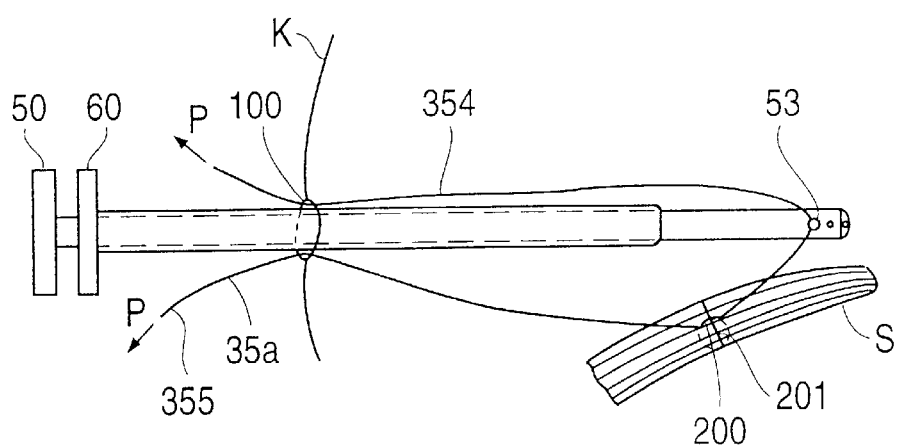
Figure 6C:
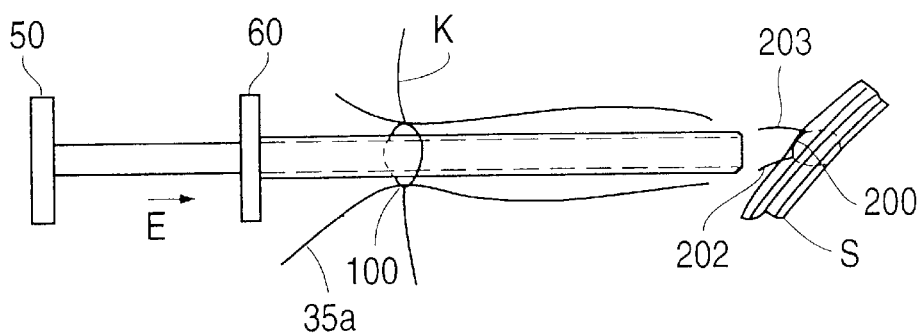
Figure 8G:
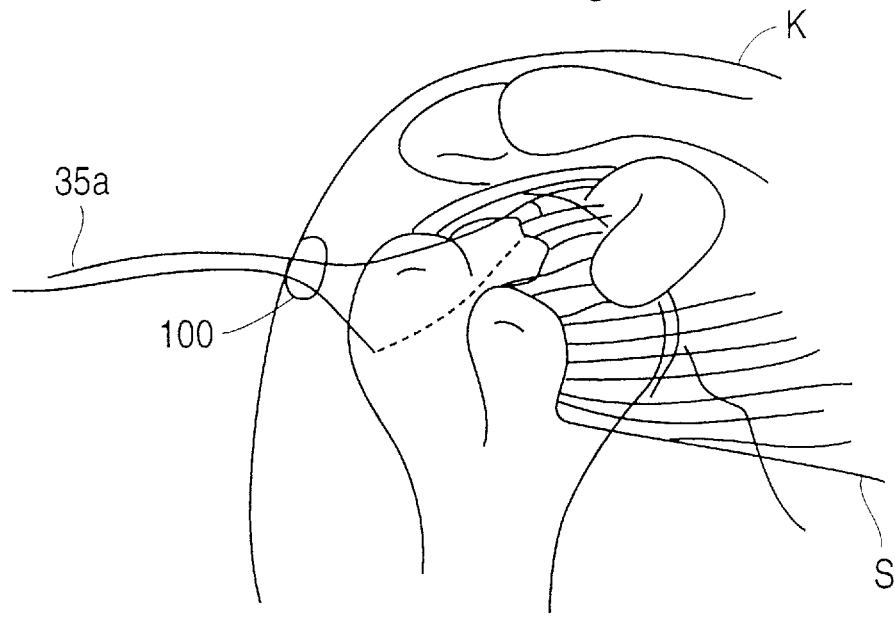
Figure 8H:
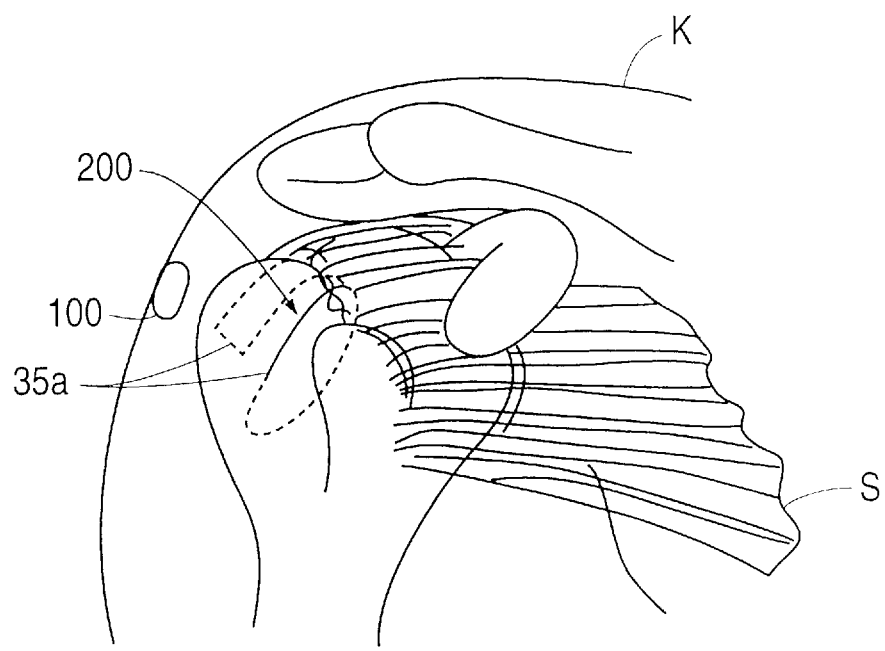

According to FIG. 8g, suture 35a laid by the bone needle is brought out with a corresponding hook from the surgical incision 100 in body K and can be knotted with the knot shifter and cutter 50, 60 according to FIGS. 5a–k as shown in FIGS. 6a–c, so that tendon S according to FIG. 8h is again attached at its original location on the bone, leaving a knot 200 in suture 35a.

Initially, a knot 200 is knotted with suture ends of suture 35 outside body K. Then suture 35a is laid through the two bores 54 at the head end of knot shifter 50, see also FIGS. 5a–5k and then the knot, which has been knotted outside the body, is pushed into the body up to the end of the tendon with the knot shifter, see FIG. 6a. Then the knot shifter and cutter is pulled out again and one end 354 of suture 35a is laid through transverse bore 53 of the knot shifter, and the other suture end 355 is held in place, see FIG. 6b, the knot shifter is then introduced once more and knot 200 is fastened in countertraction by pulling on suture ends 354, 355.

After the first knot, an additional knot is laid, so that the first knot is tight. Then sleeve 60 is advanced in the direction of arrow E, see FIG. 6c, past the knot and thus the projecting suture ends of suture 35a are cut off by cutting edge 61, see also FIG. 5a. This terminates the transarthroscopic surgical reconstruction of the tear of the rotator cuff. With the aid of the knot shifter and cutter, a lengthwise suture and O-suture can be laid and the tendon reattached to the bone in an anatomical position.

Figure 9A:
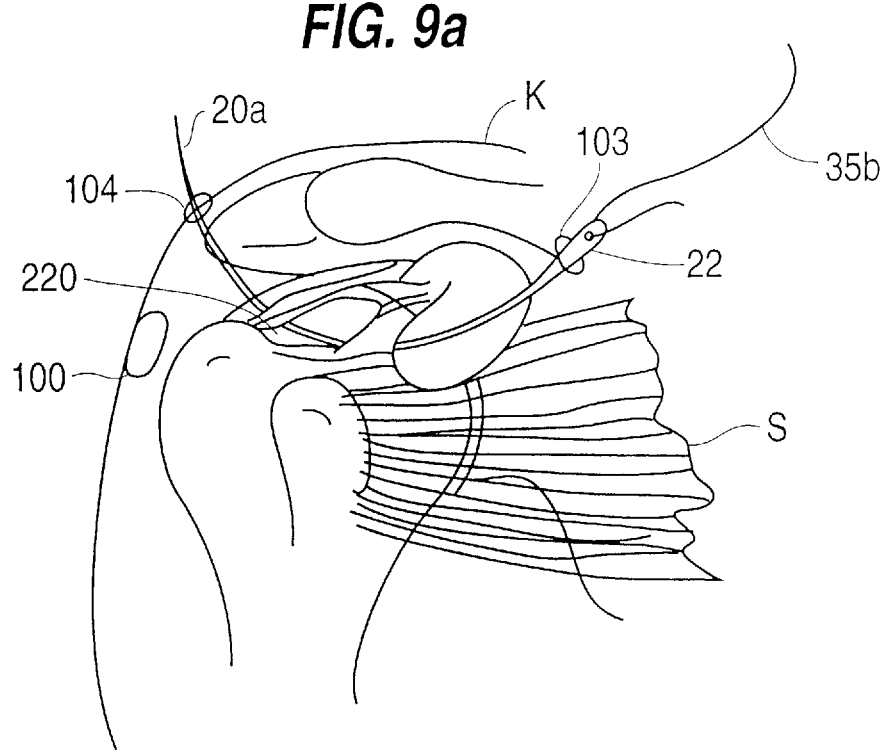
FIGS. 9a, b show the use of the instruments according to the invention in another transarthroscopic surgical reconstruction of another tear of the rotator cuff with an end-to-end tendon suture.
Figure 9B:
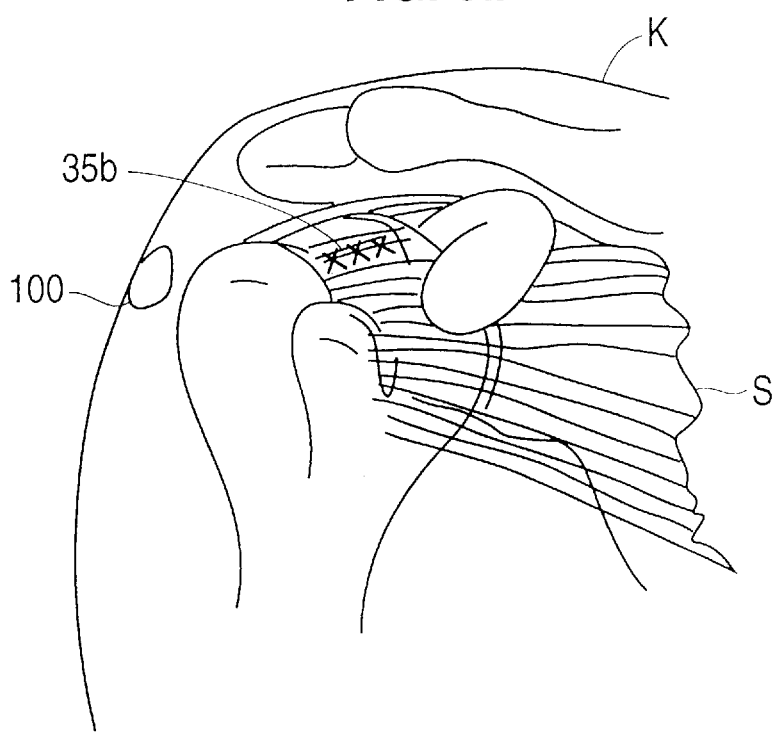

FIGS. 9a and b show another possible tear of the rotator cuff in which tendon S according to FIG. 9a has a lengthwise tear 220. After the suture has been laid with the suture layer and catcher, a needle 20a according to FIG. 2a, b is introduced in this case through incision 103 into a body K and tendon E is pierced on both sides of lengthwise tear 220. Needle 20a again leaves the body through incision 104 and tightens suture 35b in the process, said suture being fastened in eye 22 of needle 20a behind it. Now, in the manner already described, the knot in the suture made outside can be shifted using the knot shifter to the desired position in the manner already described, using the knot shifter and cutter through surgical incision 100; it is then tightened as shown in FIG. 6a–c, and this process is repeated several times until the projecting suture ends are finally cut off with the cutter. As a result, tendon S is restored to its original position.

This completes transarthroscopic surgery for reconstruction of a tear of the rotator cuff.

Therefore, in the case of a possible tear of the rotator cuff, the instruments according to the invention offer a simple possibility, with all possible variations, of performing the operation for reconstruction in a transarthroscopic manner that protects the patient, with the instruments according to the invention also being usable for other transarthroscopic surgery.

I claim:

1. A set of medical instruments for shifting and placing knots produced by surgical sutures during operations, comprising a cylindrical rod displaceable lengthwise in a cylindrical sleeve, said rod projecting at both ends beyond said sleeve, with said rod having a head end that can be retracted into said sleeve and a handle that can be struck externally at the other end of said sleeve, and said head end of said rod is designed as a knot shifter for shifting and securing a knot produced by means of a suture, and said sleeve end into which said rod can be pulled is designed as a knot cutter with a cutting edge in order to separate suture ends from knots, wherein said rod is designed as a knot shifter with a convexly rounded head end and with two continuous bores extending from the head end to accommodate a suture to a cylindrical jacket surface of the rod and wherein an additional through bore for pulling a suture through is provided in a vicinity of the head end of the rod, said through bore being located transversely with respect to a lengthwise axis of the rod.

2. A set of instruments according to claim 1, wherein the two continuous bores extending from the rounded head end are formed diametrally opposite one another at the head end of the rod relative to the lengthwise axis of the rod, with the bores being provided so that they run diagonally outward from the head end to the cylindrical jacket surface of the rod.

3. A set of instruments according to claim 1, wherein the bores are 2 to 4 mm long and have a diameter of 1 to 2 mm.

4. A set of instruments according to claim 1, wherein an entry area of the jacket surface of the rod is made rounded, at least in predetermined areas away from head end.

5. A set of instruments according to claim 1, wherein the through bore has a larger diameter than the continuous bores.

* * * * *